US012686851B2

(12) United States Patent
Yu et al.

(10) Patent No.: US 12,686,851 B2
(45) Date of Patent: Jul. 21, 2026

(54) OPTIMIZED METHOD FOR EXPANSION AND LARGE-SCALE PRODUCTION OF REGULATORY T CELLS (Tregs)

(71) Applicant: CENTRAL SOUTH UNIVERSITY, Changsha (CN)

(72) Inventors: Haibo Yu, Changsha (CN); Zhiguang Zhou, Changsha (CN)

(73) Assignee: CENTRAL SOUTH UNIVERSITY, Changsha (CN)

( * ) Notice: Subject to any disclaimer, the term of this patent is extended or adjusted under 35 U.S.C. 154(b) by 0 days.

(21) Appl. No.: 18/992,213

(22) PCT Filed: Jul. 6, 2023

(86) PCT No.: PCT/CN2023/106035
§ 371 (c)(1),
(2) Date: Jan. 8, 2025

(87) PCT Pub. No.: WO2024/008139
PCT Pub. Date: Jan. 11, 2024

(65) Prior Publication Data
US 2025/0263661 A1 Aug. 21, 2025

(30) Foreign Application Priority Data
Jul. 8, 2022 (CN) ........................ 202210805512.X

(51) Int. Cl.
*C12N 5/0783* (2010.01)

(52) U.S. Cl.
CPC ........ *C12N 5/0637* (2013.01); *C12N 2500/32* (2013.01); *C12N 2500/44* (2013.01); *C12N 2501/04* (2013.01); *C12N 2501/2302* (2013.01); *C12N 2509/00* (2013.01)

(58) Field of Classification Search
CPC .............. C12N 5/0637; C12N 2500/32; C12N 2500/44; C12N 2501/04; C12N 2501/2302
See application file for complete search history.

(56) References Cited

U.S. PATENT DOCUMENTS

2023/0174618 A1* 6/2023 Jaeger ..................... A61P 35/00
435/372.3

FOREIGN PATENT DOCUMENTS

| CN | 104278012 A | 1/2015 |
| CN | 107349219 A | 11/2017 |
| CN | 108060129 A | 5/2018 |
| CN | 108546678 A | 9/2018 |
| CN | 112458053 A | 3/2021 |
| CN | 113564117 A | 10/2021 |
| CN | 115305237 A | 11/2022 |
| WO | 2022029080 A1 | 2/2022 |

OTHER PUBLICATIONS

Doreen et al., (2015) Large-scale isolation of highly pure âuntoucheâ regulatory T cells in a GMP environment for adoptive cell therapy. J Immunother, 38(6): pp. 250-258 (Year: 2015).*
EasySepTM Human CD4+CD127lowCD25+ Regulatory T Cell Isolation Kit. Directions for Use [online]. STEMCELL Technologies, 2024 [retrieved on Jun. 17, 2025]. Retrieved from the Internet: <URL: https://cdn.stemcell.com/media/files/pis/10000000743-PIS_04.pdf>. (Year: 2024).*
Fuss et al., (Apr. 2009) Isolation of whole mononuclear cells from peripheral blood and cord blood. Current Protocols, 85(1): pp. 7.1.1-7.1.8 (Year: 2009).*
Pahwa et al., (2010) Isolation and expansion of human natural T regulatory cells for cellular therapy. J Immunol Methods, 363: 67-79 (Year: 2010).*
RoboSepTM Human CD4+CD127lowCD25+ Regulatory T Cell Isolation Kit. Directions for Use [online]. STEMCELL Technologies, 2020 [retrieved on Jun. 17, 2025]. Retrieved from the Internet: <URL: https://www.stemcell.com/media/files/pis/10000005227-PIS_00.pdf>. (Year: 2020).*
CellTrace™ CFSE Cell Proliferation Kit, for flow cytometry, Thermo Fisher Scientific, retrieved from: https://www.thermofisher.com/order/catalog/product/C34554, 2025.

* cited by examiner

*Primary Examiner* — Kara D Johnson
(74) *Attorney, Agent, or Firm* — Bayramoglu Law Offices, LLC

(57) ABSTRACT

An optimized method for expansion and large-scale production of regulatory T cells (Tregs) includes the following steps: preparing a cord blood-derived Treg-containing suspension; transferring the cord blood-derived Treg-containing suspension into a sterile tube matching with a magnetic pole, and magnetically sorting CD4$^+$CD25$^+$CD127$^-$ Tregs out; adding an expansion culture medium to Tregs carrying magnetic beads, conducting a primary culture for 1 d to 2 d, and conducting a subculture once every 1 d to 3 d, where a total culture time is 40 d to 50 d. Through one-step sorting, the method achieves very prominent cell expansion effects (shortened time and high cell viability), and increases an effective expansion time to 40 d to 50 d from 18 d. In addition, an expansion effect will not be gradually deteriorated. Thus, the method greatly increases the expansion generation number and the quantity of Tregs, and can meet the needs of clinical patients.

9 Claims, 1 Drawing Sheet

OPTIMIZED METHOD FOR EXPANSION AND LARGE-SCALE PRODUCTION OF REGULATORY T CELLS (Tregs)

CROSS REFERENCE TO THE RELATED APPLICATIONS

This application is the national phase entry of International Application No. PCT/CN2023/106035, filed on Jul. 6, 2023, which is based upon and claims priority to Chinese Patent Application No. 202210805512.X, filed on Jul. 8, 2022, the entire contents of which are incorporated herein by reference.

TECHNICAL FIELD

The present disclosure belongs to the field of cell therapy, and in particular relates to an optimized method for expansion and large-scale production of regulatory T cells (Tregs).

BACKGROUND

Regulatory T cells (Tregs) are a special T cell subset that maintains the dynamic immune homeostasis by inhibiting and regulating effector T cells. Since the isolation and identification of Tregs by Japanese scholars at the end of the last century, Tregs have become a hot topic in the research of immunity in recent years. A variety of clinical trials related to Tregs have been initiated outside China. The representative Treg therapy for graft versus host disease has confirmed the safety and efficacy of Treg therapy in treating immune diseases. However, Treg therapy for immune diseases is still blank in China. Treg therapy can restore the balance of the immune system to prevent the further damage of autoimmune responses to organs and tissues and improve or even reverse a disease state, thereby fundamentally curing an immune disease.

More and more studies have shown that the cord blood is rich in Tregs, which are mostly Naïve T cells because these Tregs are not activated by antigens. Tregs expanded in vitro have excellent functions and low immunogenicity, which brings new hope for the treatment of immune diseases. At an early stage, the team of the present disclosure has established an in vitro isolation, expansion, and functional identification method for cord blood-derived Tregs that was approved as a national invention patent (patent No.: 201710613737.4), has carried out the clinical study of treating autoimmune diabetes with cord blood-derived Tregs for the first time internationally, and has preliminarily clarified the safety and efficacy of cord blood-derived Tregs in the treatment of autoimmune diabetes. In 2019 and 2020, the Juvenile Diabetes Cure Alliance (JDCA) published the annual reports on the global technologies for treating type 1 diabetes, respectively. The "cord blood-derived Treg" therapy technology has continuously been rated as the leading technology worldwide. Globally, there is currently no clinical trial for using cord blood-derived Tregs to treat an immune disease. Tregs can be extracted from the cord blood, expanded, and then used, which takes 14 d to 21 d. A cell expansion fold each time is about 100, which can only meet the needs of 1 to 2 patients. Therefore, it is urgent to establish an optimized method for in vitro expansion of Tregs to increase the expansion generation number and quantity of Tregs, thereby meeting the needs of clinical patients.

SUMMARY

A technical problem to be solved by the present disclosure: An optimized method for in vitro expansion of Tregs is provided to overcome the deficiencies and shortcomings mentioned in the above background.

In order to solve the above technical problem, the present disclosure provides the following technical solutions:

An optimized method for expansion and large-scale production of Tregs is provided, including the following steps:

(1) preparing a cord blood-derived Treg-containing suspension;

(2) transferring the cord blood-derived Treg-containing suspension into a sterile tube matching with a magnetic pole, and magnetically sorting $CD4^+CD25^+CD127^-$ Tregs out; and (3) adding an expansion culture medium to Tregs carrying magnetic beads, conducting a primary culture for 1 d to 2 d, and conducting a subculture once every 1 d to 3 d, where a total culture time is 40 d to 50 d or more.

In the optimized method for expansion and large-scale production of Tregs, preferably, in the step (1), the cord blood-derived Treg-containing suspension is prepared through the following steps: isolating a peripheral blood mononuclear cell (PBMC) layer from cord blood, removing red blood cells with a red blood cell lysis buffer, washing, and counting; and conducting centrifugation, removing a supernatant, and resuspending.

More preferably, the resuspending includes the following steps: after the centrifugation is conducted and the supernatant is removed, resuspending cells with an Easy Buffer to produce 0.5 mL to 6 mL of a suspension with a cell concentration of $5 \times 10^7$ cells/mL.

In the optimized method for expansion and large-scale production of Tregs, preferably, in the step (2), the $CD4^+$ $CD25^+CD127^-$ Tregs are magnetically sorted out through the following specific steps: after the cord blood-derived Treg-containing suspension is transferred into the sterile tube matching with the magnetic pole, adding CD25 Positive Selection Cocktail, and incubating for 5 min; vortexing Releasable RAPIDSPHERE™ for 30 s or more until magnetic bead aggregates disappear; adding the Releasable RAPIDSPHERE™; adding a $CD4^+T$ cell enrichment antibody mixture, and incubating for 5 min; adding an Easy Buffer to 10 mL, and gently mixing 2-3 times; placing the sterile tube on the magnetic pole, and incubating for 10 min; preparing a centrifuge tube to collect $CD25^-$ cells, and pouring a liquid in the sterile tube into the centrifuge tube under the magnetic pole; removing the sterile tube from the magnetic pole, adding 10 mL of an Easy Buffer to the sterile tube, gently mixing 2-3 times, placing the sterile tube on the magnetic pole, and incubating for 5 min; adding an Easy Buffer to the initial resuspension volume with all cells on a tube wall rinsed off; adding a magnetic bead-removing buffer; adding a $CD127^{high}$-removing antibody mixture, and incubating for 5 min; adding an Easy Buffer to 10 mL, and thoroughly mixing 2-3 times; placing the sterile tube on the magnetic pole, and incubating for 5 min; and preparing a centrifuge tube to collect Tregs, and pouring a liquid in the sterile tube into the prepared centrifuge tube under the magnetic pole. The Releasable RAPIDSPHERE™ can be a releasable fastball. The Easy Buffer, e.g., EasySep™ can be simple magnetic bead for sorting.

More preferably, an amount of the CD25 Positive Selection Cocktail added is the resuspension volume×50 μL, an amount of the Releasable RAPIDSPHERE™ added is the resuspension volume×30 μL, an amount of the $CD4^+T$ cell enrichment antibody mixture added is the resuspension volume×50 μL, an amount of the magnetic bead-removing buffer added is the resuspension volume×100 μL, and an amount of the CD127$^{high}$-removing antibody mixture added is the resuspension volume×50 μL.

In the optimized method for expansion and large-scale production of Tregs, preferably, in the step (3), the Tregs carrying magnetic beads are added to a 48-well plate at a concentration of 2×10$^5$ to 8×10$^5$/mL per well, and 0.5 mL of the expansion culture medium is added to each well for culture.

Preferably, in the step (3), in volume fractions, the expansion culture medium includes 70.54% to 85.27% of a serum-free medium, 2.5% to 5% of a 4-hydroxyethylpiperazine ethanesulfonic acid buffer, 1% to 2% of a penicillin-streptomycin solution, 1% to 2% of L-glutamine, 50 μmol/L to 100 μmol/L of 2-mercaptoethanol, 0 U/mL to 1,000 U/mL of recombinant interleukin-2, 50 nmol/L to 200 nmol/L of rapamycin, and 10% to 20% of AB serum.

Preferably, in the step (3), both the primary culture and the subculture are conducted at 36° C. to 38° C. and 4% to 6% $CO_2$.

More preferably, on day 1 to day 2 after inoculation, 0.5 mL to 1 mL of the expansion culture medium and 100 U/mL to 400 U/mL of rhIL-2 are added to cells in each well, and then a culture is conducted.

More preferably, during the subculture, 0.5 mL of a medium in each well is removed, the remaining medium is thoroughly mixed with cells, cells in each well are passaged to 2 wells, and the medium is supplemented to 1 mL per well; and when the subculture is conducted a third time, the anti-CD3CD28 magnetic beads are removed, and then fresh anti-CD3CD28 magnetic beads are added with a number ratio of the magnetic beads to Tregs being 1:1.

Compared with the prior art, the present disclosure has the following beneficial effects:

1. The method of the present disclosure adopts one-step sorting and a new kit, does not require centrifugation, and has a very prominent cell expansion effect (shortened time and high cell viability). Generally, with the extension of an expansion time, an expansion effect is gradually deteriorated. However, the present disclosure not only increases an effective expansion time to 40 d to 50 d from 18 d, but also will not make an expansion effect gradually deteriorated. Thus, the method of the present disclosure greatly increases the expansion generation number and the quantity of Tregs, and can meet the needs of clinical patients.

2. Flow cytometry results of cord blood-derived Tregs produced from the expansion of the present disclosure show that, on day 18 and day 40 to day 50 of expansion, proportions of CD4$^+$CD25$^+$CD127$^-$ Tregs are 97.07±2.03% and 87.1±7.2%, respectively, and proportions of CD3$^+$CD8$^+$ Tregs are 4.69±2% and 5.2±3.6%, respectively, which meet the requirements of patients treated in clinical research. Carboxyfluorescein diacetate succinimidyl ester (CFSE) assay results show that cord blood-derived Tregs produced after the expansion can significantly inhibit the proliferation ability of aggressive T cells.

BRIEF DESCRIPTION OF THE DRAWINGS

To describe the technical solutions in the embodiments of the present disclosure or in the prior art clearly, the accompanying drawings required for describing the embodiments or the prior art will be briefly described below. Apparently, the accompanying drawings in the following description show some embodiments of the present disclosure, and a person of ordinary skill in the art may still derive other accompanying drawings from these accompanying drawings without creative efforts.

DETAILED DESCRIPTION OF THE EMBODIMENTS

Figure 1:
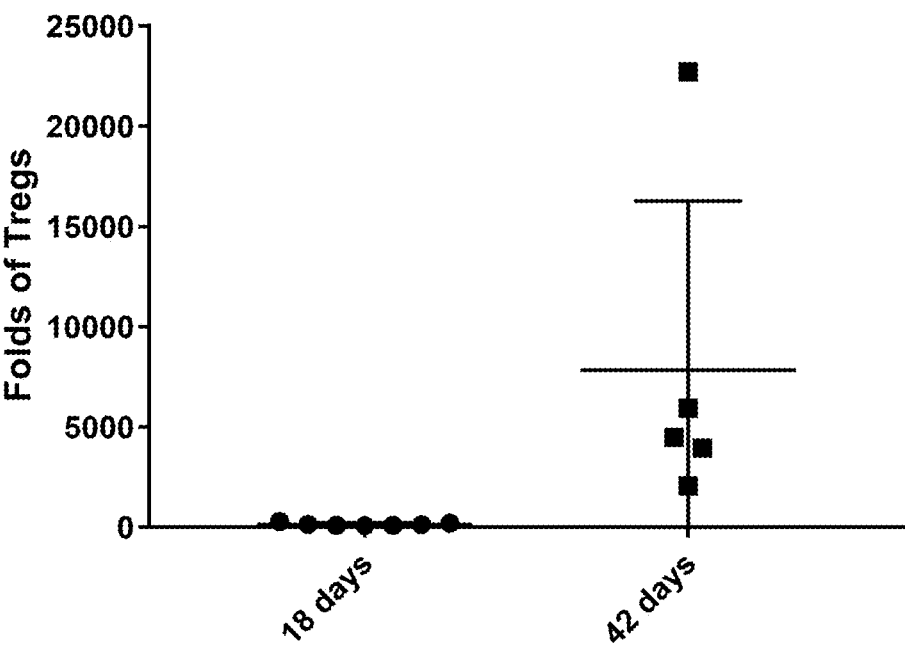
FIG. 1 shows the comparison of folds of cord blood-derived Tregs on day 18 and day 40 to day 50 of expansion.

In order to facilitate the understanding of the present disclosure, the present disclosure is described in detail below in conjunction with the accompanying drawings of the specification and the preferred embodiments, but the protection scope of the present disclosure is not limited to the following specific embodiments.

Unless otherwise defined, all technical terms used hereinafter have the same meaning as commonly understood by those skilled in the art. The technical terms used herein are merely for the purpose of describing specific embodiments, and are not intended to limit the protection scope of the present disclosure.

Unless otherwise specified, various raw materials, reagents, instruments, devices, etc. used in the present disclosure can be purchased from the market or can be prepared by the existing methods.

EMBODIMENTS

An optimized method for expansion and large-scale production of Tregs was provided. With the method, Tregs could be subjected to expanded culture and stored for treating immune-related diseases. The expansion method was as follows:

I. Preparation of Cord Blood-Derived Tregs

1. Sterilization of a cord blood bag and preparation of cord blood-derived autologous plasma: Cord blood in the cord blood bag was transferred into a 50 mL centrifuge tube and centrifuged under the following conditions: 20° C., 3,000 rpm, 10 min, +8, and −9. A resulting supernatant was collected and transferred to a new 50 mL centrifuge tube and further centrifuged under the following conditions: 20° C., 4,000 rpm, 10 min, +8, and −9. Resulting yellow clear plasma was collected, inactivated in a 56° C. water bath for 30 min, and then placed in a refrigerator for later use. The remaining cord blood was resuspended with normal saline in the same volume as the collected plasma.

2. The cord blood resuspended in normal saline was slowly added to a lymphocyte separation solution (a volume of the cord blood: a volume of the lymphocyte separation solution=1:1), and centrifugation was conducted under the following conditions: 20° C., *400 rcf to*1610 rcf, 25 min, +0, and −0. After the centrifugation was completed, the cord blood was layered. A PBMC layer was slowly and gently collected with a pipette, where a lymphocyte liquid should be pipetted as little as possible.

3. The PBMC layer was further centrifuged under the following conditions: 20° C., *580 rcf, 10 min, +8, and −9. 5 mL to 10 mL of a 10× red blood cell lysis buffer and 45 mL of sterilized water were taken and prepared into a red blood cell lysis buffer. After the centrifugation was completed, a resulting supernatant was removed, and the red blood cell lysis buffer was added. 2 min to 10 min later, 0.9% normal saline was added to 35 mL to stop the red blood cell lysis. Centrifugation was conducted under the following conditions: 20° C., *290 rcf, 10 min, +8, and −9. A resulting supernatant was removed. The steps of adding 0.9% normal saline to a specified volume, centrifugation, and removing a resulting supernatant were repeated 2–3 times.

4. After a supernatant produced after the final centrifugation was removed, resulting cells were loosened by flicking, 0.9% normal saline was added, and 10 μL of a resulting cell solution was taken for counting. 0.9% normal saline was added to the remaining cells to 40 mL. Centrifugation was further conducted under the following conditions: 20° C., *290 rcf, 10 min, +8, and −9. The counting was conducted through the following specific steps: The cell solution taken was added to an EP tube, 90 μL of trypan blue was added to the EP tube, and thorough mixing was conducted. 10 μL of a resulting mixture was taken and added to a hemacytometer, and quickly counted: (sum of numbers in four corners/4)×$10^5$ cells/mL*dilution factor. For cells on lines, cells on the upper and left lines were counted, and cells on the lower and right lines were not counted.

5. After the centrifugation was completed, a resulting supernatant was removed, and cells were resuspended with an Easy Buffer to produce 0.5 mL to 6 mL of a cell suspension with a cell concentration of 5×$10^7$ cells/mL.

6. The cell suspension produced after the resuspending was transferred into a sterile tube matching with a magnetic pole.

7. A CD25-positive selection antibody was added at an amount of the resuspension volume ×50 μL, and thorough mixing was conducted.

8. Incubation was conducted for 5 min.

9. Releasable spheres were vortexed for 30 s or more until magnetic bead aggregates disappeared.

10. The releasable spheres were added at an amount of the resuspension volume ×30 μL, and thorough mixing was conducted.

11. A CD4+T cell enrichment antibody mixture (T cell Enrichment Cocktail) was added at an amount of the resuspension volume ×50 μL, and thorough mixing was conducted.

12. Incubation was conducted for 5 min.

13. An Easy Buffer was added to 10 mL, and gentle mixing was conducted 2–3 times.

14. The sterile tube was placed on the magnetic pole without a cap.

15. Incubation was conducted for 10 min.

16. A centrifuge tube was prepared to collect CD25− cells, and a liquid in the sterile tube was poured into the centrifuge tube under the magnetic pole.

17. The sterile tube was removed from the magnetic pole, 10 mL of an Easy Buffer was added, and gentle mixing was conducted 2–3 times. The sterile tube was placed on the magnetic pole, and incubation was conducted for 5 min.

18. The steps 16 and 17 were repeated twice.

19. An Easy Buffer was added to the initial resuspension volume with all cells on a tube wall rinsed off.

20. A magnetic bead-removing buffer (Release Buffer) was added at an amount of the resuspension volume ×100 μL, and vigorous mixing was conducted 5 or more times.

21. A CD127$^{high}$-removing antibody mixture (Depletion Cocktail) was added at an amount of the resuspension volume ×50 μL, and thorough mixing was conducted.

22. Incubation was conducted for 5 min.

23. An Easy Buffer was added to 10 mL, and thorough mixing was conducted 2–3 times.

24. The sterile tube was placed on the magnetic pole, and incubation was conducted for 5 min.

25. A centrifuge tube was prepared to collect Tregs, and a liquid in the sterile tube was poured into the prepared centrifuge tube under the magnetic pole to obtain CD4+CD25+CD127− Tregs.

The above process for acquiring CD4+CD25+CD127− Tregs could adopt a EasySep™ CD4+CD25+CD127− Treg sorting kit, with brand: STEMCELL™ Technologies and Item No.: 18063.

II. Expansion of Tregs

1. Tregs were inoculated into a 48-well plate at 2×10' to 8×$10^5$/mL, 0.5 mL of an expansion culture medium including magnetic beads (a number of the magnetic beads: a number of cells=1:1) was added per well on day 0 (a formula of the expansion culture medium was shown in Table 1), and the cells were cultured at 37° C. and 5% $Co_2$.

TABLE 1

Formula of 50 mL of the expansion culture medium for cord blood-derived Tregs

| Reagent name | Company | Item No. | Volume | Final concentration |
|---|---|---|---|---|
| X-VIVO 15 w/o Gent or Phenol Red | Lonza | 04-744Q | 35.274 ml-42.69 ml | 70.54%-85.27% |
| Hepes | Hyclone | SH3023701 | 1.25 ml-2.5 ml | 2.5%-5% |
| PENICILLIN STREPTOMYCIN | Gibco | 15140122 | 0.5 ml-1 ml | 1%-2% |
| L-Glutamine solution | sigma | G7513-100ML | 0.5 ml-1 ml | 1%-2% |
| 1000X 2-Mercaptoethanol | Millipore | ES-007-E | 50 μl-100 μl | 50-100 umol/L |
| rhIL-2 | R&D | 202-IL-010 | 7.69 μl-15.4 μl | 200-400 U/ml |
| rapamycin | sigma | R8781-200UL | 1 μl-10 μl | 50-200 nmol/L |
| AB serum | Gemini | 100-512 | 5 ml-10 ml | 10%-20% |

2. On day 1 to day 2 after the inoculation (24 h to 48 h later), 0.5 mL to 1 mL of the expansion culture medium and 100 U/mL to 400 U/mL of rhIL-2 were added to cells in each well, and cells were cultured at 37° C. and 5% $CO_2$.

3. On day 3 to day 4 after the inoculation, a first passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$. After the addition, there was 1 mL of the expansion culture medium in each well, and the content of rhIL-2 added was based on 1 mL of the expansion culture medium. The amounts of rhIL-2 added in other steps were the same as the amount in this step.

4. On day 5 to day 6 after the inoculation, a second passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

5. On day 7 to day 10 after the inoculation, a third passage was conducted as follows: The anti-CD3CD28 magnetic beads in a Petri dish were removed, and then washed fresh anti-CD3CD28 magnetic beads (a number of the magnetic beads: a number of Tregs=1:1) were added. Cells were cultured at 37° C. and 5% $CO_2$.

6. On day 10 to day 11 after the inoculation, a fourth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

7. On day 11 to day 12 after the inoculation, a fifth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

8. On day 12 to day 13 after the inoculation, a sixth passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

9. On day 13 to day 14 after the inoculation, a seventh passage was conducted as follows: 0.5 mL of the expansion culture medium was removed, the remaining expansion culture medium was thoroughly mixed with cells, and cells in each well were passaged to 2 wells. An expansion culture medium including 100 U/mL to 400 U/mL of rhIL-2 was added to 1 mL, and cells were cultured at 37° C. and 5% $CO_2$.

10. The expansion was conducted according to the above method until cells stopped growing. A total culture time was about 40 d to 50 d.

In this embodiment, contents of components in the expansion culture medium for Tregs were expressed in volume fractions. A volume fraction refers to a volume proportion of each component. The expansion culture medium for Tregs included 70.54% to 85.27% of a serum-free medium, 2.5% to 5% of a 4-hydroxyethylpiperazine ethanesulfonic acid buffer, 1% to 2% of a penicillin-streptomycin solution, 1% to 2% of L-glutamine, 50 mol/L to 100 mol/L of 2-mercaptoethanol, 0 U/mL to 1,000 U/mL of recombinant interleukin-2, 50 nmol/L to 200 nmol/L of rapamycin, and 10% to 20% of AB serum.

The serum-free medium could be X-VIVO 15 w/o Gent or Phenol Red of Lonza, Item No.: 04-744Q. The 4-hydroxyethylpiperazine ethanesulfonic acid buffer could be a Hepes buffer of Hyclone, Item No.: SH3023701. The penicillin-streptomycin solution could be PENICILLIN STREPTO-MYCIN of Gibco, 15140122. The L-glutamine could be an L-glutamine solution of sigma, Item No.: G7513-100ML. The 2-mercaptoethanol could be 1000× 2-Mercaptoethanol of Millipore, Item No.: ES-007-E. The recombinant interleukin-2 could be rhrhIL-2 of R&D, Item No.: 202-IL-010. The rapamycin could be rapamycin of sigma, Item No.: R8781-200UL. Of course, the same products produced by other companies could also be adopted. The AB serum was from Gemini, USA, Item No.: 100-512.

A preparation method of the above expansion culture medium slightly varied according to the specific use. For example, when Tregs were recovered and inoculated into a plate, the components of the expansion culture medium could be thoroughly mixed in advance and then directly added to a well plate, or the components other than the recombinant interleukin-2 for the expansion culture solution could be mixed to produce a premix and then the recombinant interleukin-2 was added. Because the recombinant interleukin-2 was basically exhausted in each well during the subculture, in the passage from 1 well to 2 wells, the premix was supplemented to each well. For example, 0.5 mL of the premix was supplemented to 1 mL of a solution in each well. In this case, the corresponding recombinant interleukin-2 should be added based on the amount of the expansion culture medium: 1 mL.

Criteria for the above expansion culture test were as follows:

Cells were inoculated into a 48-well plate at $1 \times 10^6$ cells/well/mL, and an expansion culture medium including magnetic beads (a number of the magnetic beads: a number of Tregs=1:1) was added. The cells were cultured in an environment at 36° C. to 38° C. and 4% to 6% $CO_2$. Then the cell expansion was conducted according to the established expansion conditions. A formula of the expansion culture medium was as follows: 42.69 parts of a serum-free medium, 1.25 parts of a 4-hydroxyethylpiperazine ethanesulfonic acid buffer, 0.5 part of a penicillin-streptomycin solution, 0.5 part of L-glutamine, 0.05 part of 2-mercaptoethanol, 0.01154 part of recombinant interleukin-2, 0.001 part of rapamycin, and 5 parts of AB serum.

An initial number of Tregs was $1 \times 10^6$. A number of expanded Tregs was counted. The counting was conducted through the following specific steps: 10 μL of a cell suspension was taken and added to an EP tube, 90 μL of trypan blue was added to the EP tube, and thorough mixing was conducted. 10 μL of a resulting mixture was taken and added to a hemacytometer, and quickly counted: (sum of numbers in four corners/4)×$10^5$ cells/mL*dilution factor. For cells on lines, cells on the upper and left lines were counted, and cells on the lower and right lines were not counted.

An expansion fold of Tregs was 7834.4±8430.4 on day 40 to day 50 of the expansion of Tregs, and an expansion fold of Tregs was 150.6±70.3 on day 18 of the expansion of Tregs, as shown in FIG. 1.

Experiment 1: A Phenotype of Cord Blood-Derived Tregs was Stable after Expansion 1. One well of Tregs ($5 \times 10^5$ to $10 \times 10^5$) were taken, and 0.9% normal saline was added to 5 mL (room temperature). Centrifugation was conducted under the following conditions: 20° C.,*570 rcf, 5 min, +8, and −9.

2. A phenotype of Tregs was detected with a PerFix-nc Kit (Item No.: PN B10825, Beckman). This kit included the following three buffers: buffer 1: Fixative Reagent, PN B10827-75tests-liquid; buffer 2: Permeabilizing Reagent, PN B10828–75tests-liquid; and buffer 3: Final 10× Solution, PN B10829–75tests-liquid. A supernatant produced after the centrifugation was removed by a pipette tip with 50 μL to 100 μL of a liquid left, and then 5 μL of the buffer 1 and 5 μL of an Fc Block antibody were added. Shaking was conducted (moderately), and incubation was conducted at room temperature in the dark for 15 min.

3. 5 μL of each of CD3, CD4, CD25, CD127, and CD8 antibodies was added. Shaking was conducted (moderately), and incubation was conducted at room temperature in the dark for 15 min to 30 min.

4. 3 mL of the buffer 3 diluted into a working solution (buffer 3: water=1:9) was added. Centrifugation was conducted under the following conditions: 20° C., *570 rcf, 5 min, +8, and −9.

5. Flow cytometry was conducted. Flow cytometry results showed that, on day 18 and day 40 to day 50 of expansion, proportions of $CD4^+CD25^+CD127^-$ Tregs were 97.07±2.03% and 87.1±7.2%, respectively, and proportions of $CD3^+CD8^+$ Tregs were 4.69±2% and 5.2±3.6%, respectively, which met the requirements of patients treated in clinical research.

Experiment 2: Cord Blood-Derived Tregs Could Significantly Inhibit the Proliferation Ability of Aggressive T Cells after Expansion 1. CD4(+)CD25(−) aggressive T cells were recovered, and $1×10^6$ cells were taken.

2. The cells ($1×10^6$ cells) were resuspended with 1 mL of a serum-free medium.

3. 1 μL of a cell trace stock solution was added per 1 mL of a cell suspension (CellTrace™ CFSE Cell Proliferation Kit, Item No.: C34554, Thermofisher™ scientific. This kit included 10 parts of single-use bottled Cell-Trace™ CFSE (component A) and 1 part of bottled dimethyl sulfoxide (DMSO) (component B). The cell trace stock solution was a mixed solution of 18 μL of DMSO and one part of bottled CellTrace™ CFSE prepared according to the instructions of the kit for CFSE staining of cells. Details could be seen on https://www.thermofisher.com/order/catalog/product/C34554).

4. Incubation was conducted for 20 min at 37° C. in the dark.

5. 5 mL of a washing solution (serum-free medium+10% fetal bovine serum (FBS) was added.

6. Incubation was conducted for 5 min at 37° C. in the dark.

7. Centrifugation was conducted under the following conditions: 20° C., *290 rcf, 10 min, +8, and −9.

8. Cells were resuspended with a medium (serum-free medium+10% FBS) pre-warmed at 37° C.

9. One well of Tregs were taken, subjected to magnetic bead removal, counted, and centrifuged under the following conditions: 20° C., *290 rcf, 10 min, +8, and −9.

10. $1×10^6$ Tregs were resuspended with a medium (serum-free medium+10% FBS) pre-warmed at 37° C.

11. CD4(+)CD25− T cells and Tregs were co-cultured in a 96-well plate with a number ratio of the CD4(+)CD25− T cells to the Tregs being 1:1, 2:1, and 4:1 (in each well, there was 200 μL in total, and 3 μL of magnetic beads was added). A CD4(+)CD25− T cell group treated with CFSE alone was set as a negative control group, and a CD4(+)CD25− T cell group treated with CFSE (magnetic bead stimulation) was set as a positive control group.

12. An inhibitory function of cord blood-derived Tregs was detected by flow cytometry.

Figure 2:
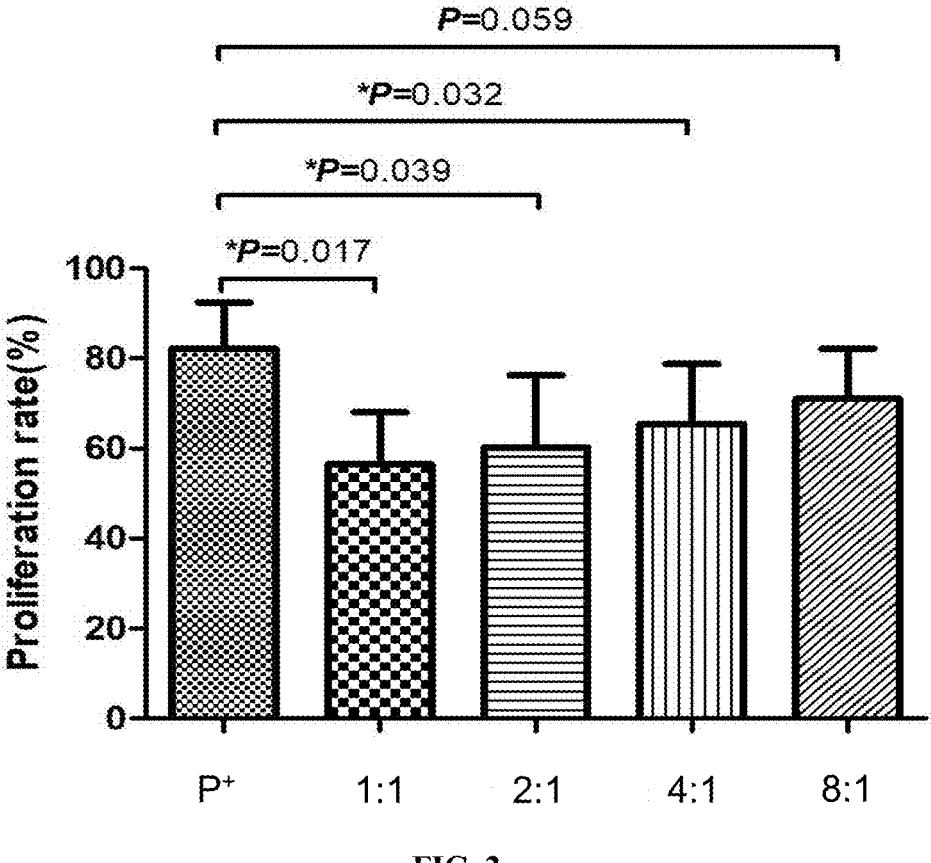
FIG. 2 shows the results of CFSE-based functional identification for cord blood-derived T cells on day 18 of expansion.

13. Results of the CFSE experiment showed that, when CD4(+) CD25−T cells and Tregs were co-cultured in number ratios of 1:1, 2:1, 4:1, and 8:1, the proliferation rates of CD4(+) CD25− T cells were 56.5±11.6%, 60.2±16.1%, 65.4±13.4%, and 71.1±11.2%, respectively. The results indicated that the expanded cord blood-derived Tregs could significantly inhibit the proliferation ability of aggressive T cells, as shown in Tables 2 to 6 and FIG. 2.

TABLE 2

| | | Expansion folds of cord blood-derived Tregs on day 18 of expansion | | | |
|---|---|---|---|---|---|
| Sample | Initial cell source | Number of initial umbilical blood mononuclear cells (UBMCs) (10^8) | Number of Tregs on day 0 (10^6) | Number of Tregs on day 18 (10^8) | Expansion fold (based on cell numbers) |
| 1 | Cryopreserved | 1.42 | 1.4 | 1.3 | 93 |
| 2 | Cryopreserved | 3.25 | 3.4 | 4.96 | 146 |
| 3 | Fresh | 2.58 | 1.29 | 3.58 | 283 |
| 4 | Cryopreserved | 2.5 | 1.52 | 1.46 | 96 |
| 5 | Cryopreserved | 3.2 | 2.25 | 4.6 | 204 |
| 6 | Fresh | 2.77 | 3.55 | 4.71 | 133 |
| 7 | Fresh | 2.33 | 4.6 | 2.7 | 99 |
| Mean ± standard deviation | | 2.58 ± 0.62 | 2.57 ± 1.29 | 3.33 ± 1.54 | 150.57 ± 70.33 |

TABLE 3

| | Phenotypic identification results for cord blood-derived T cells on day 18 of expansion | |
|---|---|---|
| Sample | CD3 + CD4 + CD25 + CD127 − Tregs(%) | CD8 + T cells(%) |
| 1 | 93.4 | 7.58 |
| 2 | 98.2 | 5.93 |
| 3 | 99 | 6.56 |
| 4 | 96.2 | 2.71 |
| 5 | 95.8 | 3.05 |
| 6 | 98.7 | 2.77 |

TABLE 3-continued

| | Phenotypic identification results for cord blood-derived T cells on day 18 of expansion | |
| --- | --- | --- |
| Sample | CD3 + CD4 + CD25 + CD127 − Tregs(%) | CD8 + T cells(%) |
| 7 | 98.2 | 4.23 |
| Mean ± standard deviation | 97.07 ± 2.03 | 4..69 ± 2.00 |

TABLE 4

| | | Number of initial UBMCs (10^8) | Number of Tregs on day 0 (10^6) | Expansion fold (based on cell numbers) |
| --- | --- | --- | --- | --- |
| Sample | Initial cell source | | | |
| 1 | Cryopreserved | 3.25 | 3.4 | 3960 |
| 2 | Fresh | 2.58 | 1.29 | 22709 |
| 3 | Cryopreserved | 2.5 | 1.52 | 2064 |
| 4 | Cryopreserved | 3.2 | 2.25 | 5945 |
| 5 | Fresh | 2.77 | 3.55 | 4494 |
| Mean ± standard deviation | | | | 7834.4 8430.5 |

Expansion folds of cord blood-derived T cells on day 40 to day 50 of expansion

TABLE 5

| | Phenotypic identification results for cord blood-derived T cells on day 40 to day 50 of expansion | |
| --- | --- | --- |
| Sample | CD3 + CD4 + CD25 + CD127 − Tregs(%) | CD8 + T cells(%) |
| 1 | 78.9 | 2.49 |
| 2 | 89.8 | 3.74 |
| 3 | 92.6 | 9.28 |
| Mean ± standard deviation | 87.1 ± 7.2 | 5.2 ± 3.6 |

TABLE 6

Results of CFSE-based functional identification for cord blood-derived T cells on day 40 to day 50 of expansion

| | 1 | 2 | 3 | Mean ± standard deviation |
| --- | --- | --- | --- | --- |
| P+ | 70.4 | 87.6 | 88.6 | 82.2 ± 10.2 |
| 1:1 | 44.6 | 67.8 | 57.0 | 56.5 ± 11.6 |
| 2:1 | 42.7 | 74.4 | 63.4 | 60.2 ± 16.1 |
| 4:1 | 50.8 | 77.0 | 68.5 | 65.4 ± 13.4 |
| 8:1 | 59.2 | 81.4 | 72.6 | 71.1 ± 11.2 |

In summary, the method of the present disclosure adopts one-step sorting and a new kit, does not require centrifugation, and has a very prominent cell expansion effect (shortened time and high cell viability). Generally, with the extension of an expansion time, an expansion effect is gradually deteriorated. However, the present disclosure not only increases an effective expansion time to 40 d to 50 d from 18 d, but also will not make an expansion effect gradually deteriorated. Thus, the method of the present disclosure greatly increases the expansion generation number and the quantity of Tregs, and can meet the needs of clinical patients.

What is claimed is:

1. An optimized method for expansion of regulatory T cells (Tregs), comprising the following steps:

(1) preparing a cord blood-derived Treg-containing suspension;

(2) transferring the cord blood-derived Treg-containing suspension into a sterile tube, adding CD25 Positive Selection Cocktail, and incubating for 5 min;

vortexing releasable streptavidin-coated magnetic particles for 30 seconds or more until magnetic bead aggregates disappear;

adding the releasable streptavidin-coated magnetic particles and a CD4⁺T cell enrichment antibody mixture to the transferred cord blood-derived Treg-containing suspension, and incubating for 5 min;

placing the sterile tube on a magnetic pole, and incubating for 10 min; pouring a first liquid in the sterile tube into a first centrifuge tube;

placing the sterile tube on the magnetic pole, and incubating for 5 min; adding a magnetic bead-removing buffer to the incubated sterile tube; then adding a CD127$^{high}$-removing antibody mixture to the incubated sterile tube, and incubating for 5 min;

placing the sterile tube on the magnetic pole, and incubating for 5 min; pouring the incubated liquid in the sterile tube into a second centrifuge tube to obtain CD4⁺CD25⁺CD127⁻ Tregs; and (3) adding an expansion culture medium to Tregs, conducting a primary culture for 1 d to 2 d, and conducting a subculture once every 1 d to 3 d, wherein a total culture time is 40 d to 50 d, wherein in the step (3), in volume fractions, the expansion culture medium comprises 70.54% to 85.27% of a serum-free medium, 2.5% to 5% of a 4-hydroxyethylpiperazine ethanesulfonic acid buffer, 1% to 2% of a penicillin-streptomycin solution, 1% to 2% of L-glutamine, 75 μmol/L to 100 μmol/L of 2-mercaptoethanol, 0 U/mL to 1,000 U/mL of recombinant interleukin-2, 50 nmol/L to 200 nmol/L of rapamycin, and 15% to 20% of AB serum.

2. The optimized method for the expansion of the Tregs according to claim 1, wherein in the step (1), the cord blood-derived Treg-containing suspension is prepared through the following steps: isolating a peripheral blood mononuclear cell (PBMC) layer from cord blood, removing red blood cells with a red blood cell lysis buffer, washing, and counting; and conducting centrifugation, removing a supernatant, and resuspending.

3. The optimized method for the expansion of the Tregs according to claim 2, wherein the resuspending comprises the following steps: after the centrifugation is conducted and the supernatant is removed, resuspending cells to produce 0.5 mL to 6 mL of a suspension with a cell concentration of 5×10⁷ cells/mL.

4. The optimized method for the expansion of the Tregs according to claim 1, wherein 50 μL of the CD25 Positive Selection Cocktail is added per each 1 mL of a resuspension volume, an amount of the Releasable streptavidin-coated magnetic particles added is the resuspension volume×30 μL, an amount of the CD4$^+$T cell enrichment antibody mixture added is the resuspension volume×50 μL, an amount of the magnetic bead-removing buffer added is the resuspension volume×100 μL, and an amount of the CD127$^{high}$-removing antibody mixture added is the resuspension volume×50 μL.

5. The optimized method for the expansion of the Tregs according to claim 1, wherein in the step (3), the Tregs carrying the magnetic beads are added to a 48-well plate at a concentration of 2×10$^5$ to 8×10$^5$/mL per well, and 0.5 mL of the expansion culture medium is added to each well for culture.

6. The optimized method for the expansion of the Tregs according to claim 1, wherein in the step (3), both the primary culture and the subculture are conducted at 36° C. to 38° C. and 4% to 6% $CO_2$.

7. The optimized method for the expansion of the Tregs according to claim 6, wherein on day 1 to day 2 after inoculation, 0.5 mL to 1 mL of the expansion culture medium and 100 U/mL to 400 U/mL of rhIL-2 are added to cells in each well, and then the primary culture is conducted.

8. The optimized method for the expansion of the Tregs according to claim 7, wherein during the subculture, 0.5 mL of a medium in each well is removed, a remaining medium is thoroughly mixed with cells, the cells in each well are passaged to 2 wells, and the medium is supplemented to 1 mL per well; and when the subculture is conducted a third time, anti-CD3CD28 magnetic beads are removed, and then fresh anti-CD3CD28 magnetic beads are added with a number ratio of the magnetic beads to the Tregs being 1:1.

9. The optimized method for the expansion of the Tregs according to claim 6, wherein during the subculture, 0.5 mL of a medium in each well is removed, a remaining medium is thoroughly mixed with cells, the cells in each well are passaged to 2 wells, and the medium is supplemented to 1 mL per well; and when the subculture is conducted a third time, anti-CD3CD28 magnetic beads are removed, and then fresh anti-CD3CD28 magnetic beads are added with a number ratio of the magnetic beads to the Tregs being 1:1.

* * * * *